US006235046B1

(12) United States Patent
Gerdt

(10) Patent No.: US 6,235,046 B1
(45) Date of Patent: May 22, 2001

(54) PASSIVE PHOTONIC EYE DELIVERY SYSTEM

(76) Inventor: David W. Gerdt, 3054 Plank Rd., North Garden, VA (US) 22959

( * ) Notice: Subject to any disclaimer, the term of this patent is extended or adjusted under 35 U.S.C. 154(b) by 0 days.

(21) Appl. No.: 09/234,921

(22) Filed: Jan. 21, 1999

Related U.S. Application Data

(60) Provisional application No. 60/072,022, filed on Jan. 21, 1998.

(51) Int. Cl.[7] .................................................... A61N 5/06
(52) U.S. Cl. ............................ 607/88; 607/91; 607/93; 600/26
(58) Field of Search ................... 606/7–9; 607/88–92; 128/898, 395; 362/103–106; 600/26–27

(56) References Cited

U.S. PATENT DOCUMENTS

| | | | |
|---|---|---|---|
| 5,163,426 | * 11/1992 | Czeisler et al. | 128/395 |
| 5,167,228 | * 12/1992 | Czeisler et al. | 128/395 |
| 5,176,133 | * 1/1993 | Czeisler et al. | 128/395 |
| 5,304,212 | * 4/1994 | Czeisler et al. | 607/88 |
| 5,447,527 | * 9/1995 | Waldman | 607/88 |
| 5,447,528 | * 9/1995 | Gerardo | 607/88 |
| 5,465,737 | * 11/1995 | Schachar | 128/898 |
| 5,503,637 | * 4/1996 | Kyricos et al. | 607/88 |
| 5,545,192 | * 8/1996 | Czeisler et al. | 607/88 |
| 5,562,719 | * 10/1996 | LOpez-Claros | 607/88 |
| 5,824,024 | * 10/1998 | Dial | 607/88 |
| 5,919,217 | * 7/1999 | Hughes | 607/90 |

OTHER PUBLICATIONS

Eugene Hecht, "Optics", Second Edition, Addison–Wesle Publishing Company, Inc., 1990.*

* cited by examiner

*Primary Examiner*—John Mulcahy
*Assistant Examiner*—Ahmad Farah
(74) *Attorney, Agent, or Firm*—Sheldon H. Parker

(57) ABSTRACT

A device for the application of artificial light to a user's retina is disclosed. A light source leads to a light focusing member that generates a light stream at, at least one transmission angle, to the user's retina, preventing the light from coming in contact with the user's fovea. In one embodiment, the light focusing member is a light ring containing a plurality of apertures around an outer periphery with light exiting through the apertures in a plurality of streams at a transmission angle. A vision aperture within the light ring has a periphery less than the outer periphery and is on a direct axis with the user's fovea to enable the user to maintain vision during chronotherapy. The light source can be distanced from the light focusing member and connect by a light transfer member, such as a optic fiber. In another embodiment, the light focusing member can be the frame of a pair of eyeglasses having lenses to enable user vision. The light source can be either proximate the apertures around the frame or distanced from the glasses with the light being transmitted from the light source to the glasses by a transfer member.

20 Claims, 7 Drawing Sheets

PASSIVE PHOTONIC EYE DELIVERY SYSTEM

This application claims benefit of provisional No. 60/072,022, filed, Jan. 21, 1998.

BACKGROUND OF THE INVENTION

1. Field of the Invention

The invention discloses a safe, economical system for changing the body's circadian rhythm through the incorporation of fiber optics in combination with a light source.

2. Brief Description of the Prior

The internal systems of all animals follow a cycle regulated by hormones. These cycles are daily, monthly, and yearly and are controlled by changes in length of light vs. dark. This is commonly referred to as circadian rhythm and affects the body's rhythmic repetition of certain functions, including sleep. The internal biological Circadian clock cycles once in about 25 hours. In healthy people, the ordinary day/night visual exposure to sunlight is sufficient to reset the circadian dock each day. This mechanism is clever and simple, requiring only set point. Such a regulatory method is insufficient to make as simple a mechanical device as a house thermostat, which requires two set points, operate correctly. It is thus possible, in healthy individuals, to use strong broad band light to force melatonin suppression, thereby phase shifting their Circadian clock. Physical and emotional problems can occur in people who loose part or all of their circadian function or are unable to receive a dose of optical radiation sufficient to reset their clock.

Those who live in the Northern latitudes suffer more from clock regulation problems because the winter months the daily dose of sunshine is not sufficient for their body's internal clock to maintain synchronicity with day/night cycles. This lack of regulation can result in disruption of sleep, decreased attention span, gastrointestinal disturbances, irritability, headaches, reduced immunity, clinical depression, carbohydrate cravings, weight gains, reduced work productivity, social withdrawal, to name a few. Because many people have few or no problems during the summer, this condition is called "Seasonally Affected Disorder" (SAD).

Air travel poses increasingly common problems as the circadian cycle is upset if more than two times zones are crossed in one day. Commonly known as "jet-lag," this problem is caused because the normal clock is only reset about one hour per day. It is well known in the field that one's circadian clock can be reset by administering carefully timed doses of bright light separated by careful avoidance of the same light at other specified times.

When light is administered to the eye at specific times relative to the circadian cycle, the therapy is often called chronotherapy. Chronotherapy has been developed to treat diseases or conditions through the use of light and, for these purposes, includes controlling the Circadian Rhythm, by advancement or retardation, as it relates to the internal circadian clock. The current conventional system is a light box with eyecups. The box is highly reflective, diffused white, like the inside of an integrating sphere and contains a source, or sources, which fill the box or cavity with light. The source is shielded to prevent a direct path from the source to the retina of the eye. Therefore, the eye sees a uniform illumination field, usually broad wavelength band white, rather than a specific narrow wavelength bank or line of light. It is possible to spectrally filter a portion of the source, but the sources are generally weak and too little of the filtered light reaches the retina for a chronotherapeutic effect. With very bright sources, a light box would be versatile. light boxes are currently used for treating Seasonally Affected Disorder (SAD) and it is likely that they can be used for shifting the phase of the Circadian Rhythm. Light boxes are little used except by those who are desperate. The general population is unwilling to use a light box for the required 100 to 200 minutes per day and, especially since no other use of the eyes is possible during light box chronotherapy.

The search for a method of passive ocular chronotherapy was motivated by a desire to enable a user to undergo chronotherapy while not otherwise limit eye function. This type of chronotheral)y is dubbed "passive" because the eyes may be used for other activities, such as watching television, reading a book, performing various sight guided tasks, or driving while receiving photonic medication. One form of passive chronotherapy is to place a chronotherapeutic subject into a specifically built, light filled room, in which the subjects are exposed to carefully filtered light. These rooms are very expensive and one or more are being built at Harvard with their primary goal being to test spectral response intensity and exposure (time) effects on chronotherapy.

The disclosed device overcomes the problems associated with passive chronotherapy but providing an inexpensive, portable device that overcomes the above disadvantages.

SUMMARY OF THE INVENTION

A device for the application of artificial light to a user's retina is disclosed. The device has a light source leading to a light directing member that generates a light stream at, at least one transmission solid angle, to the user's retina. The transmission angles prevent the light from coming in contact with the user's fovea. In one embodiment, the light directing member is a light ring containing a plurality of apertures around an outer periphery. Light from the light source exits through the apertures in a plurality of streams, with each of the streams exiting at a transmission angle formed by the center line of the light stream and the surface of the directing member. The transmission angle can also be created by a lens positioned at the aperture. A vision aperture within the light ring has a periphery less than the outer periphery and is on a direct axis with the user's fovea. This enables the user to maintain vision during chronotherapy. The light source can be distanced from the light-directing member, being transmitted from the light source to the focusing member through at least one light transfer member. The first end of the light transfer member is placed proximate the light directing member and a second end of the transfer member is placed proximate the light source.

Preferably, the light transfer member is an optic fiber having a core and cladding. The device can have one optic fiber tips for each aperture or the optic fibers can be split to enable one fiber to transmit light to multiple apertures. Alternatively a single clad fiber can be positioned adjacent the apertures and the cladding being removed from the fiber proximate the apertures. Removal of the cladding enables the light to transmit through the aperture.

One method of determining the solid angle of the light stream angle is through the following formula:

$$n.a.=\sqrt{n^2_{cl}-n^2_{co}}$$

where n.a. equals sin θ, θ is half the angle projected by said stream of light, $n_{cl}$ is the refractive index of said fiber cladding, and $n_{co}$ is the refractive index of said fiber core of said fiber. Thus, when n.a.≈0 the light stream is collimated and when n.a ≈ 1 the light stream exits at an angle of about 90 degrees.

The light source can be moveably affixed to a first end of a rail and with the second end of the light transfer member affixed to a second end of the rail. Preferably, the light source can move along the rail in relation to the light transfer member. Filters are preferably placed on the rail between the light source and the light transfer member in a manner that enables the filters to be changed.

In another embodiment, the light directing member can be the frame of a pair of eyeglasses having lenses to enable user vision. The light source can be either proximate the apertures around the frame or distanced from the glasses with the light being transmitted from the light source to the glasses by a transfer member.

The disclosed device can be used alone or in combination with filter glasses to phase shift a user's circadian clock. The light application device is used for a predetermined period based on known chronotherapy procedures. The filter device used, based on predetermined periods of time to known in chronotherapy, to the inhibit production of melatonin. Alternating the application of light and a wavelength blocking filter causes the user's circadian clock to phase shift, thereby relieving problems associated with a lack of synchronicity between said user's circadian clock and natural day/night cycles.

BRIEF DESCRIPTION OF THE DRAWINGS

The advantages of the instant disclosure will become more apparent when read with the specification and the drawings, wherein.

DETAILED DESCRIPTION OF THE INVENTION

Figure 1:
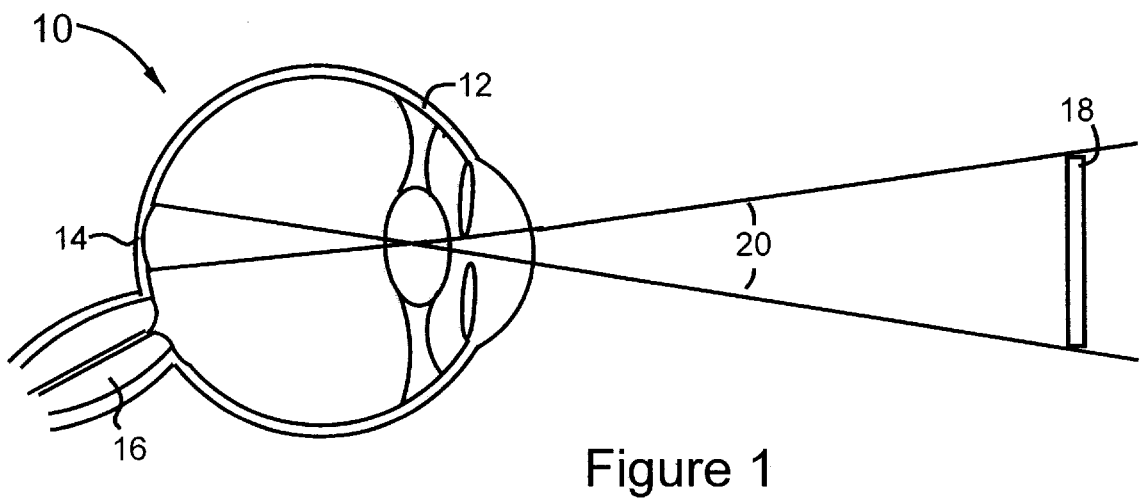
FIG. 1 is a side view of light entering the eye on a direct axis, thereby contacting the fovea.

There are many benefits that can be achieved from controlling the internal circadian clock, including relief from sleep disorders and seasonal depression. The performance of people working or living long hours in artificial environments, such as nuclear power control rooms and submarine crews, can be greatly improved by providing controlled day/night cycles. The artificial administration of full spectrum, high intensity light will also alleviate the effects of jet lag by purposefully losing synchronicity by an amount equal to the times zones being crossed. The suppression of melatonin will also reduce the tiredness encountered in long distance car and truck drivers, pilots, and military personnel.

In a world becoming increasingly accessible, inter global business communication is increasing, not only through travel but real time communication with computers and faxes. When travel is required, many corporations will allot an additional two days adjustment time in for overseas travel, costing the corporation additional funds per executive trip. Even real time communication with overseas markets causes substantial employee down time.

Currently sleep disorders are treated with hypnotic drugs, such as sleeping tablets, alternative herbal remedies, special pillows, and beds. These, however, only force or encourage the user to sleep at a certain time, and do not address either the Circadian Clock or the need for sunlight associated with SAD.

In otherwise healthy people, a bright, broadband light is sufficient for both the treatment of SAD and the programmed phase shifting of the body's internal clock. The disclosed invention uses the fact that an narrow bank source of light is sufficient to suppress melatonin, thereby synchronizing, or phase shift, the circadian clock. Further, the disclosed system also uses the fact that narrow band optical notch filters are known to be sufficient to quench the important wavelength even in bright sunlight. The eye is photochemical system where different receptors have different sensitivities to different colors of light. The most sensitive region of the spectrum is in the green near 555 nm. It is known that the Circadian response does not occur in the rods or cones of the retina, but rather in the ganglia. From the standpoint of design it makes sense that the most intense color of sunlight, green, would be sufficient to set the Circadian dock The eye is then a simple system which, besides being used for normal vision, is also used for resetting the Circadian clock by the only natural source of periodic light, the sun. The photochemical reaction, which takes place in the ganglia, has a wavelength of about 435 nm.

The realignment of the internal body clock is well known treatment for the above problems, as well as conditions not listed herein. The use of phase shifting, using ocular exposure to environmental light is set forth below and is found at http:/www.uwrf.edu/~cg04/physiology/CR-7/html.

| # time zones crossed | Days after transport | Get bright light | Avoid bright light |
|---|---|---|---|
| | | Travel Westward | |
| 3–6 | 1–3 | Late evening | Early morning |
| 7–9 | 1 | Late evening/ early afternoon | Late evening |
| | 2–4 | Late evening | Early morning |
| | 1–2 | Afternoon | Late |
| 10–11 | 3–5 | Evening | afternoon/evening |

-continued

| # time zones crossed | Days after transport | Get bright light | Avoid bright light |
|---|---|---|---|
| 12 | 1 | Early afternoon | Early morning Late afternoon and evening |
|  | 2 | Late afternoon and early evening | Late evening |
|  | 3–5 | Evening Travel Eastward | Early morning |
| 3–5 | 1–2 | Late morning | Early morning |
| 6–8 | 1 | Early afternoon | Morning |
|  | 2 | Midday | Early morning and midmorning |
|  | 3–4 | Midmorning | Early morning |
| 9 | 1 | Mid-to-late afternoon | Morning and early afternoon |
|  | 2 | Midday | Early and midmorning |
|  | 3–4 | Late morning | |
| 10–12 | Same as listed for 12 | time zones westward | Early morning travel |

FIG. 1 illustrates how an object, in the direct line of sight, is viewed by the eye 10. In this figure, the line of sight 20 is a straight line and the image of the object 18, viewed on a direct axis, is reflected directly onto the fovea centralis retinae 14. The fovea 14 is defined as a "tiny pit, about 1 degree wide, in the center of the macula lultea, which in turn presents an extremely small depression (foveola) containing rod like elongated cones; it is the area of dearest vision, because here the layers of the retina are spread aside, permitting light to fall directly on the cones." *Dorlands Illustrated Medical Dictionary*, W. B. Saunders Company, Philadelphia Pa., 1988. Thus, an object viewed on a direct access provides the clearest view of that object by removing the shielding provided by the retina 12. While providing viewing benefits under normal circumstances, the direct exposure of bright light to the cones at the fovea 14, can cause damage to these unprotected cones, in extreme cases temporarily or permanently eliminating direct axis vision.

Figure 2:
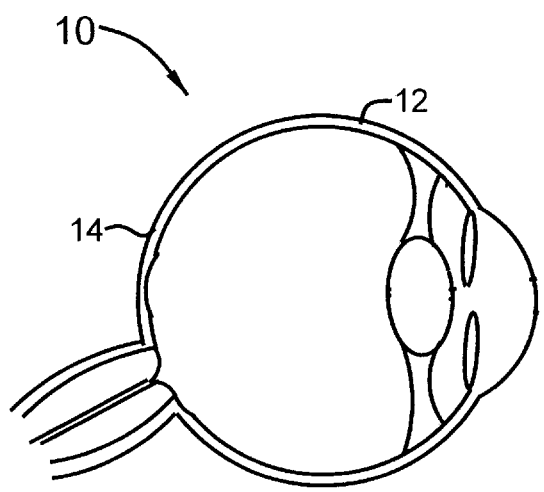
FIG. 2 is a side view of light entering the eye on an indirect axis, thereby contacting the retina.

To safely apply the light required for effective chronotherapy, the light must not move along the direct axis but rather "off center" as illustrated in FIG. 2, avoiding direct contact with the sensitive cones of the fovea 14. Avoidance of direct light exposure to the cones not only protects the user's fovea 14 from damage, but also enables the user to maintain normal vision during use of the device. This is due to the light being placed not along the direct axis, reflecting on the fovea 14, but rather angled to terminate at the retina 12. The angling of the light also enables the intensity of the source of light to be increased dramatically without damaging the user's eyes of affecting the direct line vision. This enables the user to read, watch TV or participate in other activities without being inconvenienced, or temporarily blinded.

The disclosed device is designed for minimum annoyance to the wearer. Photons of specific wavelength are delivered to the eye in flux densities near zero at the fovea and much higher at retinal regions away from the fovea. Not only is the convenience of the disclosed device increased dramatically over prior art devices, it reduces the negative physical reactions as well. Physical reactions range from inconvenience, it is impossible for someone to read while a light is shined directly into their eyes, to mild discomfort, the temporary, localized blindness caused by a flash photo. More severe physical reactions can be encountered, such as the extreme discomfort and disorientation and nausea encountered during interrogations where the interrogators surround the subject in darkness except for a blinding light flashed in the person's eyes. The equivalent adverse reactions were duplicated with the initial circadian light rings, which included light directed to the fovea. To resolve the problem of disorientation, further testing revealed that the elimination of light directed to the fovea not only eliminates the disorientation and nausea but enables the user to maintain vision along the direct axis.

Figure 3:
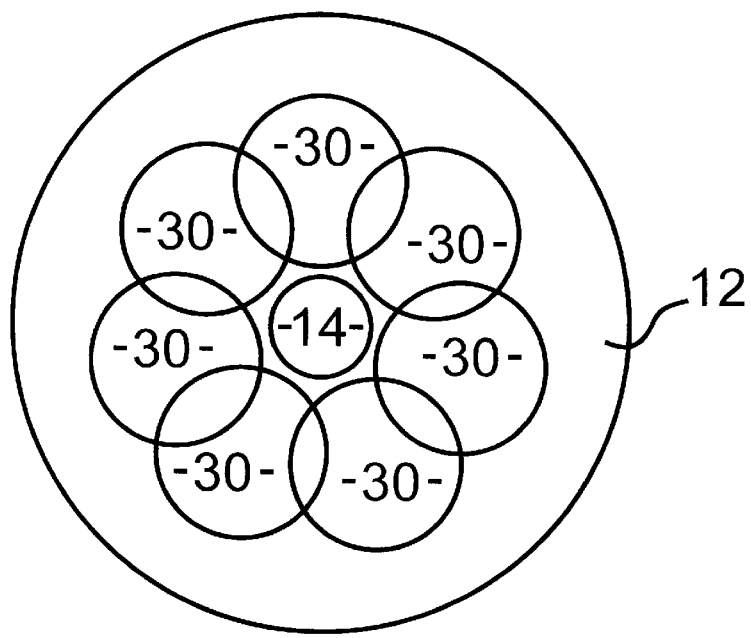
FIG. 3 is a front view of the circle of light surrounding the fovea.

The disclosed ring light device delivers the appropriate amount of light to the retina with little or no impairment to the user's direct line vision. The disclosed light ring approach provides the advantages of chronotherapy without using the traditional light box approach but incorporating light rings into glasses. The preferred pattern of light intensity is illustrated in FIG. 3 wherein light pattern surrounds, but does not contact the fovea 14. The light pattern, shown in this figure as light circles 30, are in contact with the retina 12 while not exposing the fovea 14 to light.

Figure 16:
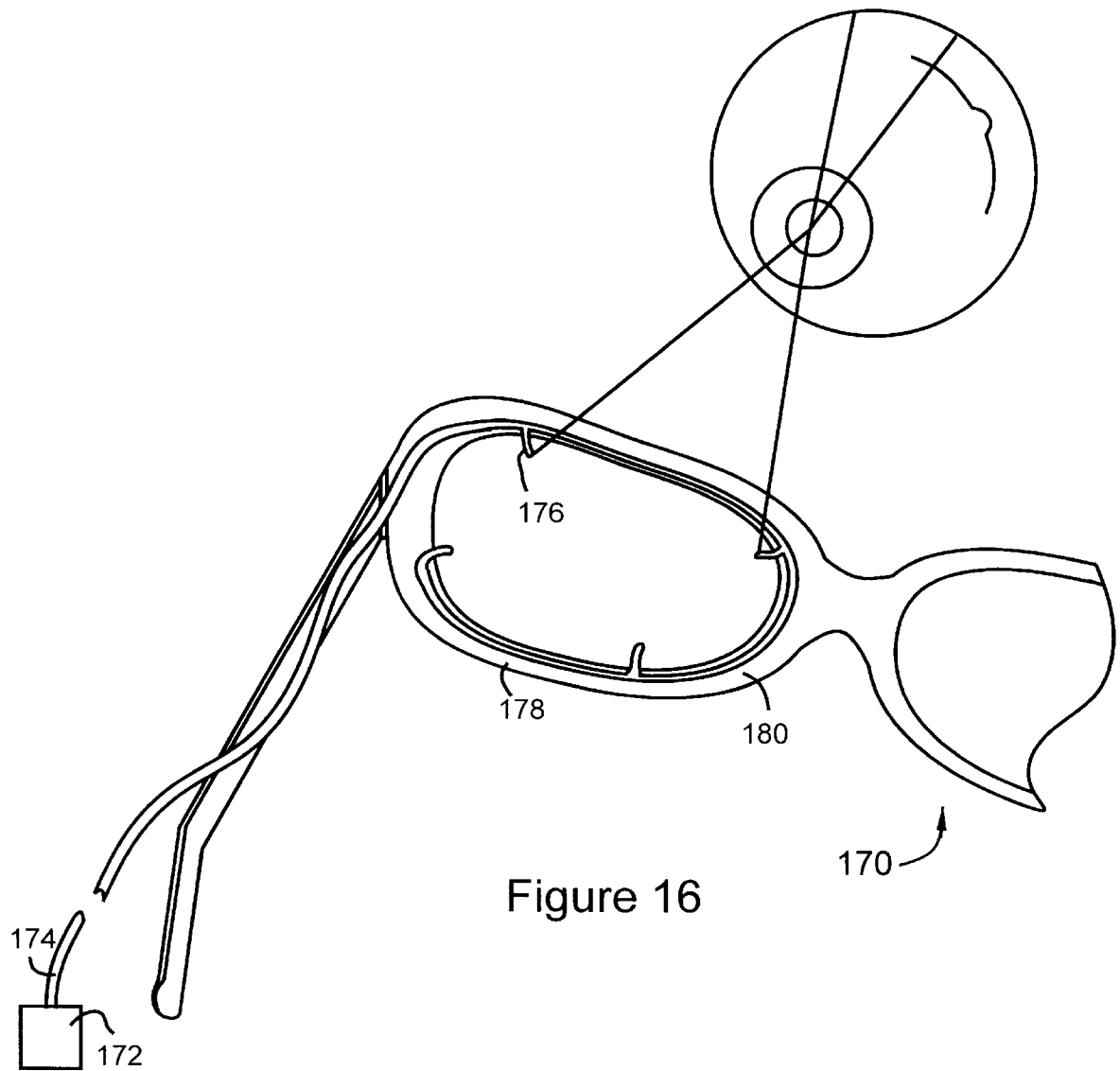
FIG. 16 is a perspective of an additional embodiment of the disclosed light directing method incorporated into a pair of glasses.

In one embodiment, the connection between the light ring and the light source was manufactured of bent, multi-strand, optical fiber. The fiber was polymethyl methocrylate, about 2 mm in diameter, with a very thin (approximately 50 $\mu$m) coating of a fluorinated polymer to serve as cladding. The fibers were configured by heating the fiber and then bending it to a specific predetermined angle. The fibers were then embedded into a clear, optical polymer block so that each end pointed out the same block face. A silicone rubber mold was constructed which both held the bent optical fiber in position and formed the block. Then the other free ends were then each pigtailed to an LED, with one power supply sourcing all the LEDs. This is illustrated in FIG. 16 wherein the tube 200, leading to the light ring, comprises individual LEDs 202 pigtailed to the end of each individual fiber 204. By affixing individual LEDs 202, the color and intensity of each light stream, or cone, can be varied as required. The unit incorporating using this technology was constructed with each fiber at the bundle end coupled to a very bright red LED. The unit was held up to the eye so that the red light of the LEDs flooded most of the eye. As LEDs are not currently commercially available at the precise wavelength, about 530 to 540 mm, and do not have sufficient brightness over most of the visual spectrum, the LEDs require specific design and manufacturing. This requires establishing the exact LED wavelength required to produce the desired brightness and spectrum visibility. Additionally, the method used to pigtail the fibers into the LEDs must be precise as most current methods further reduce the available intensity. For this method to work effectively and provide a clear, distortion free central visual area, thereby avoiding the orientation problem mentioned heretofore, optimal conditions are required. Precise pig tailing, in combination with clear fibers and precise wavelength, enable maximum and effective use of this technology. LEDs are currently not available in all colors and the color is, in many cases, important as far as maximizing a chronotherapeutic effect which limits the "across the board" use of this embodiment.

Figure 4:
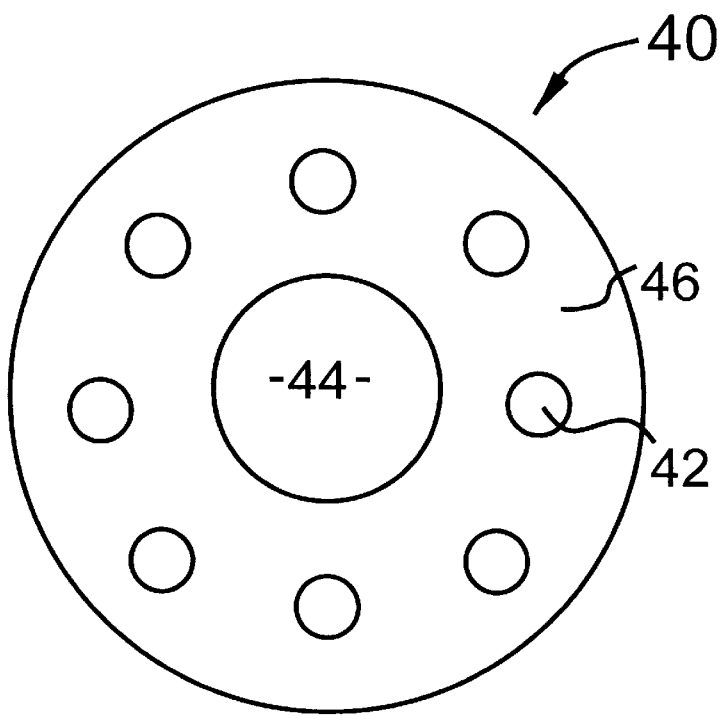
FIG. 4 is a top view of one embodiment of a light ring.

With the ability to provide a unit that is readily commercially available in mind, a portable, simple, inexpensive, and effective method was sought to easily allow for adjustment to the user's circadian dock. The disclosed device, when placed near the eye delivers light to the retina while enabling an unobstructed direct axis viewing area. Light is delivered to the light ring by a light transfer member, such as a fiber optic bundle, or optical wave guide or guides, with the light being sourced by a variety of means such as light bulbs, light emitting diodes, arc lamps, and others. The disclosed ring light/arc lamp device is capable of delivering the precise wavelength for maximum clock phase advance or retardation. To accomplish the desired light pattern, a ring light 40, illustrated in FIG. 4, was devised. The ring light 40 is provided with multiple light apertures 42 placed along its face 46. The center 44 is left open and, when placed over the user's eye, is aligned with the axis of vision, directing the light emitting from the apertures 42 to the retina 12 rather than the fovea 14. The illustrated ring light 40 or light directing member, is shown as an example of the aperture 42 placement and number and other ring light configurations will become apparent to those skilled in the art.

Figure 6:
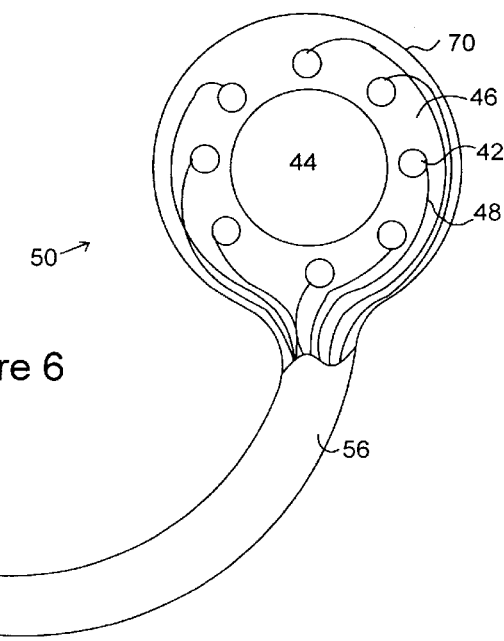
FIG. 6 is a top, cutaway view of one construction of one embodiment of the light ring.
Figure 5:
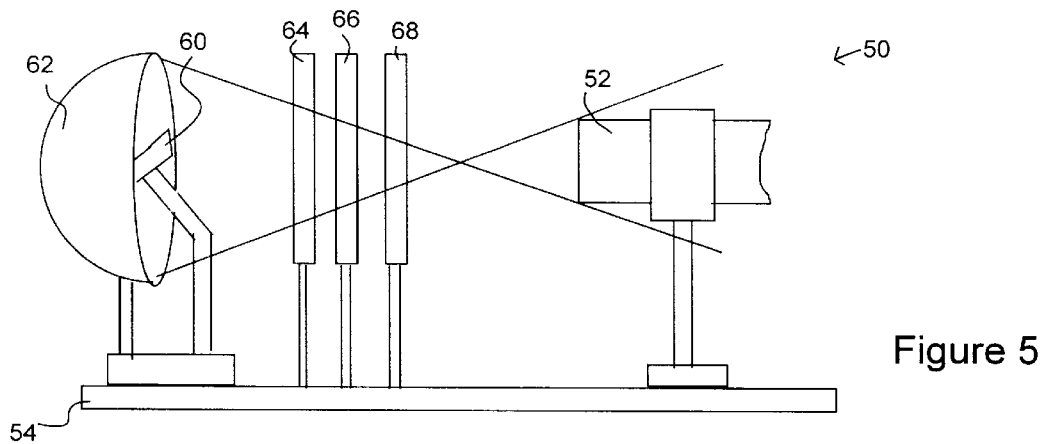
FIG. 5 is a side view of one embodiment of the light and filter base unit.
Figure 7:
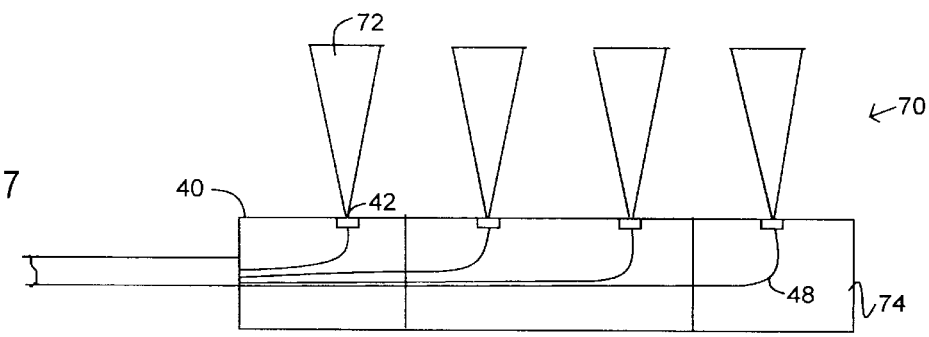
FIG. 7 is a cutaway side view of the light ring that shows the resulting light dispersion.

The embodiment illustrated in FIGS. 5 and 6 has been proven effective in altering the circadian clock in humans. The specifically designed fiber bundle ring light assembly 50 uses small ring lights that are formed by bifurcating each fiber, thereby cutting in half the number of fibers required and reducing the diameter of the transfer cord 56. The bifurcated and bundled fibers are covered with a transfer cord 56 to prevent breakage, kinking and generally maintain the fibers in a neat, easy to use package. The light receiving end 52 of the transfer cord 56 is flooded with light from a mini-metal arc halide lamp 60 affixed to an optical rail 54. A reflector 62 behind the lamp 60 helps to increase light intensity to the bundle end 52. The lamp 60 is very bright and has a relatively long focus so the optical filtering devices 66 and 68 can be placed in the sourcing path. The optical rail 54 aligns and maintains the lamp 60, reflector 62, filters 64, 66, and 68, and fiber bundle 52, in the desire, preset position. Although any of the foregoing can move along the stage 54, it is preferable, to maintain appropriate angling and reduce costs, that only the lamp 60/ reflector 62 combination move. Preferably filters include a heat mirror 64, spectral filter 68, and optional neutral density filter 66. The heat mirror 64 filters out ultraviolet light to prevent its passage into the eye as well as minimizing the amount of heat passing on to the remaining filters 66 and 68. The heat mirror 64 has a dicloride coating, or its equivalent, which absorbs the heat and protects the subsequent filters from heat damage. As the range of movement on the rail 54 is generally extremely narrow, the neutral density filter 66 is used for setting the gross intensity, enabling fine intensity adjustments to be obtained by moving the lamp 60 slight distances along the rail 54. It is possible to eliminate the density filter 66, in situations where the rail 54 has a length sufficient to enable the gross and fine intensities to be adjusted by moving the lamp 60 along the rail 54 length. The spectral filter 68 enables narrow band, broad band, cut-on, cut-off, polarization, line, or other final filtering in order to adjust the spectral content of light reaching the eye. It is preferable that all the forgoing filters be easily replaced to vary intensities, spectrums, etc. When the circadian treatments are being used on people who have lost their sight but not their circadian docks, both the density filter 66 and the spectral filter 68 can be eliminated as the photochemical properties lie in the ganglia and not the cone rods. The foregoing rail, lamp and filter design is for example only and any equivalent arrangement will be come obvious to those skilled in the art.

Figure 8:
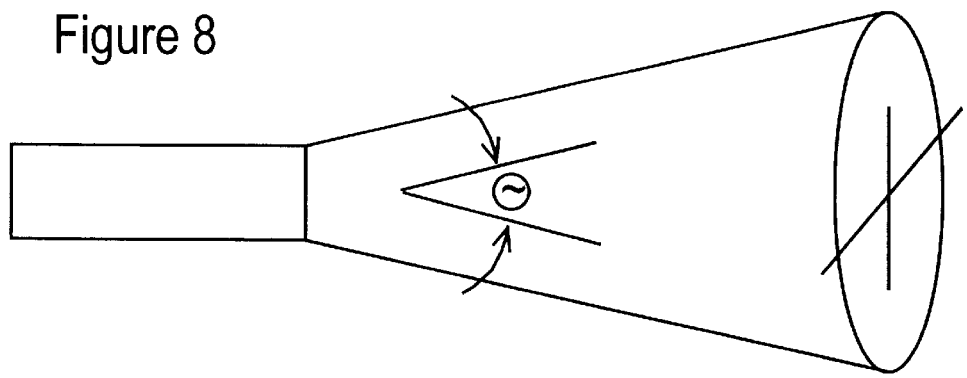
FIG. 8 is a side view of the dispersal angle of one embodiment of the invention.

The ring 70 in FIG. 6 has optic fibers 48 connected to each of the apertures 42. The fibers 48 are bundled and run down the coated transfer cord 56 to the bundle end 52. A side view of the light ring 70, as seen in FIG. 8, illustrates the fibers 48 leading to the apertures 42 thereby forming light illumination cones 72. The illustrated illumination cones 72 show the divergence of the light, which can be varied through the attachment of lenses, in accordance with the formulas set forth hereinafter, or by other methods known to these skilled in the art. The fibers 48 are contained in the base 74 of the light ring 40 and can be prevented from movement within the base 74 through use of molded channels, or other securing means. Although the fibers 48 can optionally remain loose within the base 74, the ends must be securely affixed to the apertures 42 to prevent the angle of the light cones 72 from shifting or the fiber 48 from dropping out of the aperture 42.

Figure 9:
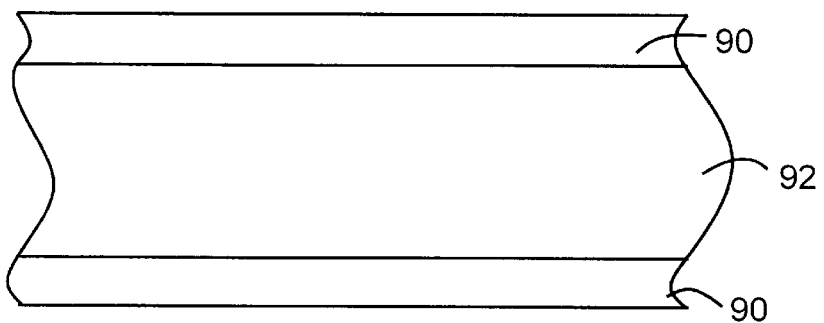
FIG. 9 is a cutaway side view of an encased fiber for use with the instant invention.
Figure 15:
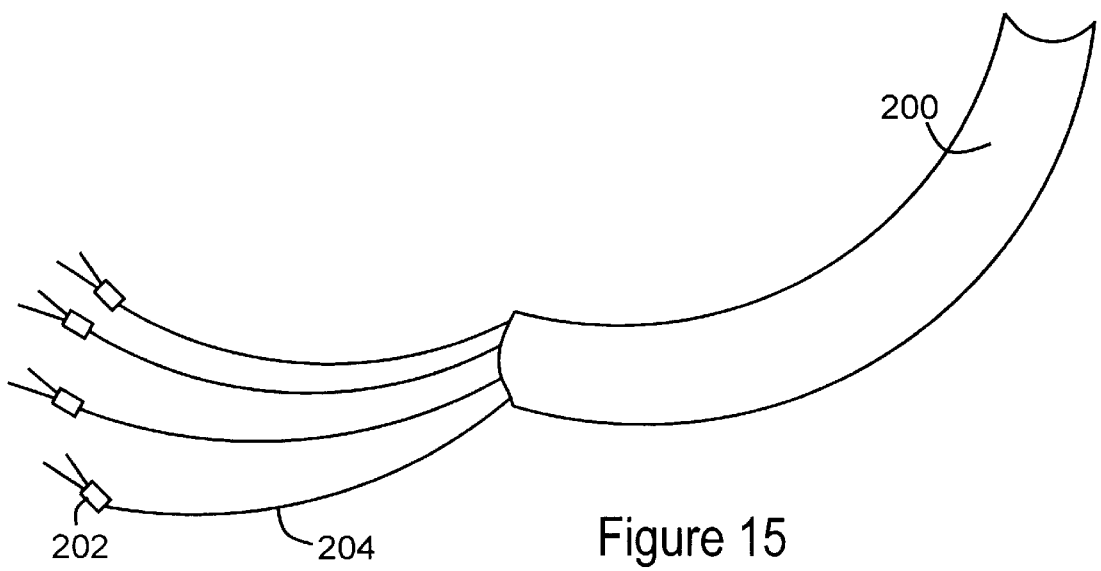
FIG. 15 is a cutaway view of the fibers and tube of an alternate embodiment of the invention.

One way the divergence can be controlled is by using the following the following equations. The numerical aperture is represented by n.a. where n.a. equal sin θ and θ is half the solid angle projected by the light stream, or cone, as illustrated in FIG. 9.

$$n.a. = \sqrt{n^2_{cl} - n^2_{co}}$$

where $n_{cl}$ is the refractive index of the cladding 90 and $n_{co}$ is the refractive index of the core 92 of the fiber, as illustrated in FIG. 9. By varying the n.a. between 0 and 1, the divergence of the resulting light ranges from collimated to maximum divergence. The formula: n.a.≈0 produces a collimated light stream; by changing 0 to ½, the light stream is broadened to a divergent stream having an exiting angle of about 45 degrees. Maximum divergence is reached by using the n.a.≈1, producing an exiting angle of about 90 degrees.

Figure 10:
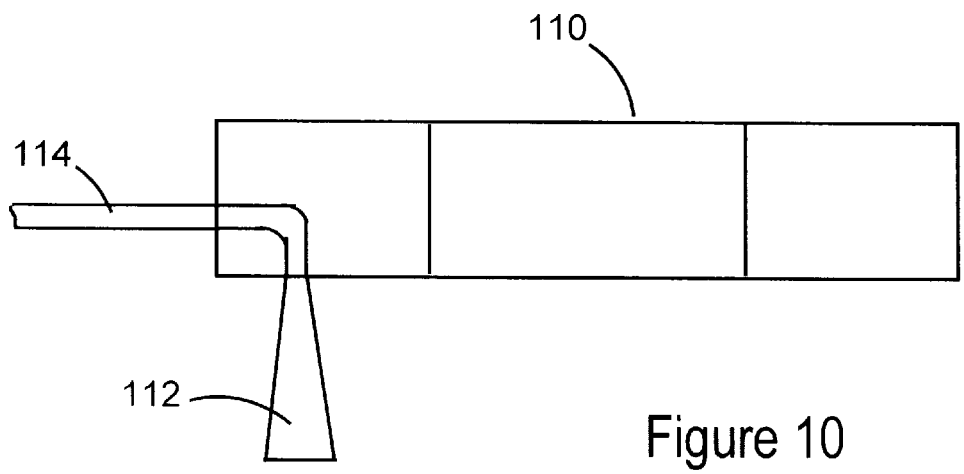
FIG. 10 illustrates the cone of illumination angle with a 90-degree exit angle.
Figure 11:
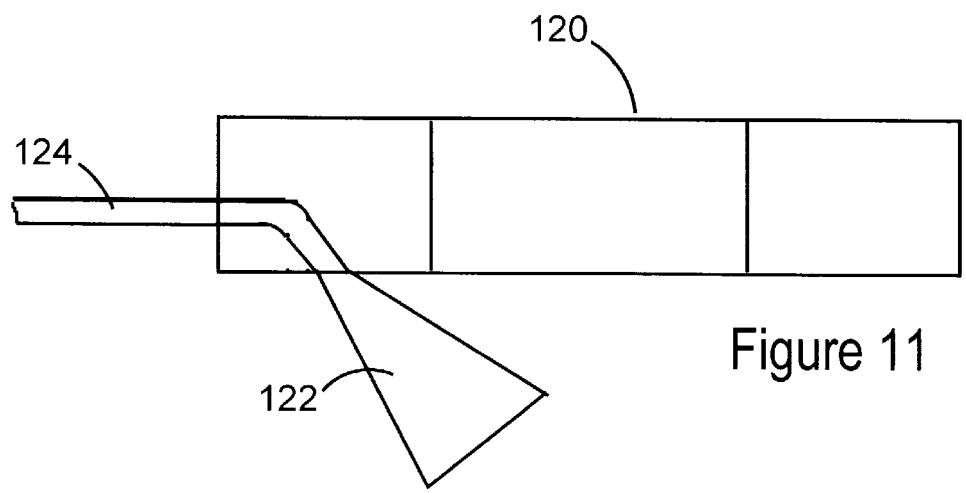
FIG. 11 illustrates the cone of illumination angle with a 105-degree exit angle.
Figure 12:
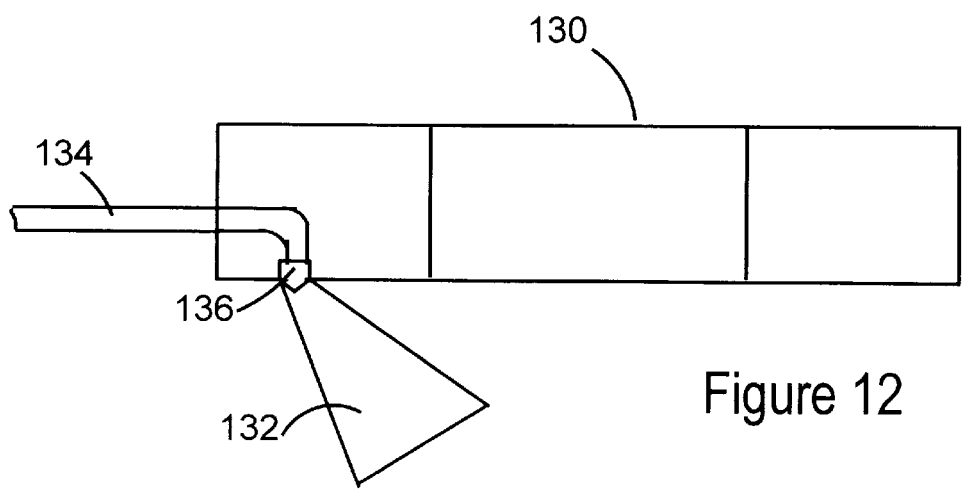
FIG. 12 illustrates the cone of illumination angle with a lens to aid in beam cone formation.

On low divergence fibers, the illumination axis can be angled with respect to the ring light housing axis. This is illustrated in FIGS. 10–12 wherein the angle of exit on the fiber has been changed, thereby producing solid angled illumination cones. In FIG. 10, the fiber 114 exits at approximately a 90-degree solid angle from the angle of entry into the ring light 110, thereby producing a cone 112 at approximately 90 degrees from the ring light 110. In FIG. 11, the angle of exit of the fiber 124 has been altered to about a 105 degrees from point of entry into the ring light 120, thereby angling the light stream 122. In FIG. 12, a lens 136 is affixed to the fiber 134 to modify the transmission angle of the light stream 132. Therefore, although the fiber 134 is placed at a 90-degree angle from the point of entry, the lens 136 causes the cone 132 to be solid angled at a different angle, depending upon the construction of the lens 132. In the preferred embodiment, the lens 132 would be removable to allow for varied cone angling using the same fiber/ring light configuration.

Figure 13:
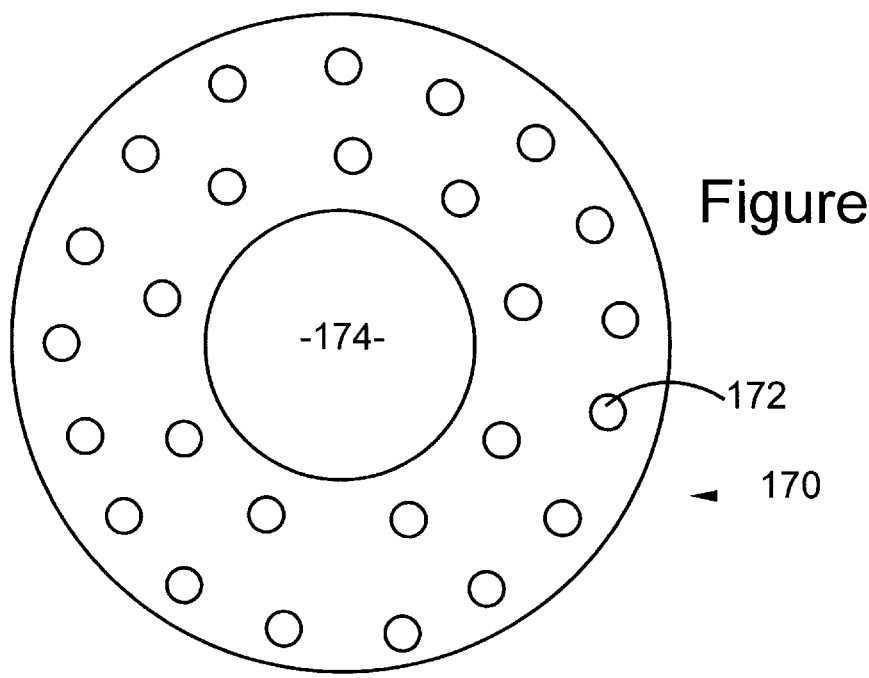
FIG. 13 is a top view of an alternate placement of light apertures.

FIG. 13 illustrates an alternate embodiment of the light ring technology wherein light ring 170 contains dual rows of apertures 172 surrounding the center opening 174. When manufacturing, dual rows of apertures, care must be taken to ensure the center opening 174 has a sufficient diameter to provide the user with adequate visibility. The determining factor between single and dual rows of apertures is one of manufacturing costs versus ability to control the cone of illumination.

Figure 14:
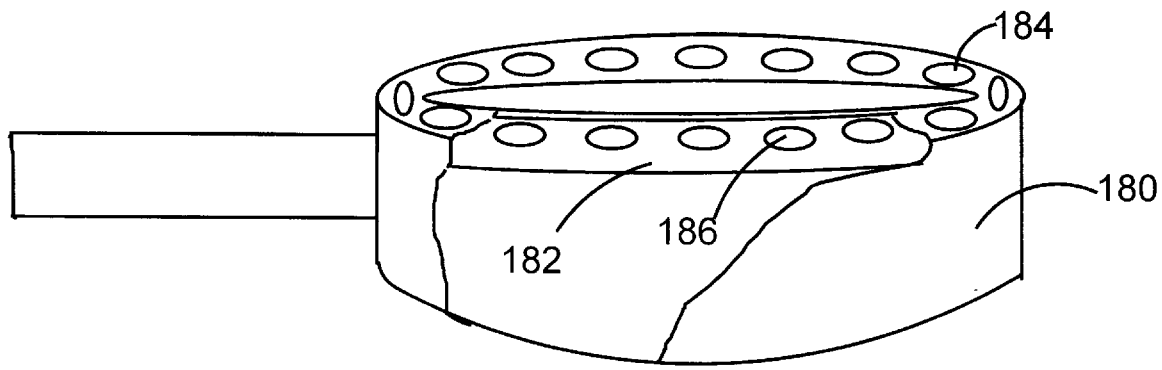
FIG. 14 is a cutaway side view of a light ring using a single fiber.

In FIG. 14 an alternate light method is utilized wherein a single fiber 182, contained within a casing as illustrated in FIG 10, is placed proximate the apertures 184 and adhered to the light ring 180. The casing covering the fiber 182 adjacent each aperture 184 is removed to expose the fiber 182 only in the light areas 186. This permits the light to escape the casing only at the location of each aperture 184.

In applying this technology to lightweight delivery glasses 170, as illustrated in FIG. 16, the power source 172 is maintained in the user's pocket. Alternatively, if a sufficiently small power source is economically feasible, the power source can be placed along the earpiece of the glasses. The optic fiber 714 is attached to the power source 172 and split at the end into lit ends 176. The optic fiber 174 is embedded into the plastic frame 180 and lenses 178 of the glasses 170, thereby maintaining the lit ends 176 in the appropriate position. The optic fiber 174 can be a single strand, which is split or coupled, or multiple strands, which end at the lit ends. There are several ways to split the single strand to form multiple ends and these will be evident to those skilled in the art. The light source 172 can be a battery powered LED, high intensity light bulb, or any of technology as disclosed above.

To further enhance the phase shift, filter glasses can be used incorporating filters that restrict the passage of light for a narrow band of the spectrum. Wrap-around glasses are used in the treatment of retinosis pigmentosis, a condition where the eye becomes hyper-sensitive to common bright light. For this particular use, the filter restricts the intensity of all regions of the environmental light, like neutral gray sunglasses. Another type of filter used is an optical filter called a "cut-on" filter, or "blue blocker." This filter blocks out the wavelengths transmitting blue while enabling the longer wavelengths to pass through. "Blue blocker" filters, by blocking the blue spectrum, turn blue to black while all other colors appear yellow.

The optimal filter for blocking the wavelengths associated with the circadian clock is known as a notch filter. This filter restricts the passage of light for only a narrow band of the spectrum in the wavelength range of about 435. Blocking this wavelength serves to restrict the melatonin production, enabling, if used in combination with the foregoing light applications, the user to override the body's circadian clock by artificially altering the day/night ratio. By blocking a narrow wavelength, such as a 10 nanometer band, from the environmental band of 300 nanometers, only minuscule color changes are encountered. This alleviates the problems related to color perception, as encountered with the blue blockers, and creates consequently less annoyance for the user.

The combination of the disclosed light application and filter glasses provides the user with a new ability to overcome the problems associated with SAD and other problems associated with circadian rhythms. Both the light application glasses and the filter glasses can be worn during activities, thereby freeing the person to function in a normal environment while phase shifting the internal clock.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A chronotherapy device for the application of artificial light to a user's eye, said device having a light source and a light directing member proximate a user's eye, said light directing member transmitting a light stream, said light stream capable of being directed at, at least one predetermined transmission solid angle, to the retina of the user's eye, said angle preventing said light from scattering as well as from coming in contact with the user's fovea.

2. The device of claim 1 wherein said transmission angle is the angle formed by the center line of said light stream and the surface of said directing member.

3. The device of claim 1 wherein said light directing member is a light ring containing a plurality of apertures around an outer periphery, light from said light source exiting through said plurality of apertures in a plurality of streams, each of said plurality of streams being at one of said at least one transmission solid angle.

4. The device of claim 3 further comprising a vision aperture, said vision aperture having a periphery less than said outer periphery and being on a direct axis with said user's fovea, thereby enabling said user to maintain vision during said chronotherapy.

5. The device of claim 4 wherein said light focusing member is a frame of a pair of eye glasses and said vision aperture are the lenses of said glasses, said lenses enabling visual equity about equal to standard glasses.

6. The device of claim 3 wherein said light source is distanced from said light directing member, said light being transmitted from said light source to said directing member through at least one light transfer member, a first end of said light transfer member being proximate said light directing member and a second end of said light transfer member being proximate said light source.

7. The device of claim 6 wherein said light transfer member is at least one optic fiber, said optic fiber having a core and cladding.

8. The device of claim 7 wherein said optic fiber is split, thereby enabling one fiber to transmit light to multiple apertures.

9. The device of claim 7 wherein said transmission angle is created by a lens positioned at said aperture.

10. The device of claim 7 wherein said light stream angle is determined by the formula $$n.a. = \sqrt{n_{cl}^2 - n_{co}^2}.$$

where:

n.a. equal sin θ,

θ is half the angle projected by said stream of light, $n_{cl}$ is the refractive index of said fiber cladding, and $n_{co}$ is the refractive index of said fiber core of said fiber, wherein when n.a.≈0 said light stream is collimated and when n.a.≈1 said light stream exits at an angle of about 90 degrees.

11. The device of claim 7 wherein said fiber optic is a single clad fiber positioned adjacent said apertures, said cladding being removed from said fiber proximate said apertures.

12. The device of claim 11 wherein said light source is proximate said apertures around said light directing member.

13. The device of claim 11 wherein said light source is distanced from said glasses, light being transmitted from said light source to said light directing member by a light transfer member.

14. The device of claim 4 wherein said light source is moveably affixed to a first end of a rail and said second end of said light transfer member is affixed to a second end of said rail, said light source moving along said rail in relation to said second end of said light transfer member.

15. The device of claim 14 further comprising filters, said filters being between said light source and said second end of said light transfer member.

16. The device of claim 15 wherein said filters are removably affixed to said rail.

17. A chronotherapy system for the application of artificial light to a user's retina, said system having:

a light directing member, said light directing member generating a light stream, said light stream capable of being directed at, at least one transmission angle, to the retina of the user's eye, said angle preventing said light from coming in contact with the user's fovea, said light stream angle being determined by the formula $$n.a. = n_{cl}^2 - n_{co}^2$$

where:
- n.a. equals sin θ,
- θ is half the angle projected by said stream of light,
- $n_{cl}$ is the refractive index of said fiber cladding, and
- $n_{co}$ is the refractive index of said fiber core of said fiber,
- when n.a.≈0 said light stream is collimated and when n.a.≈1 said light stream exits at an angle of about 90 degrees,
- a light source, said light source being distanced from said light focusing member,
- at least one optic fiber, said optic fiber having a core and cladding and transmitting said light from said light source to said directing member, a first end of said fiber being proximate said light directing member and a second end of said fiber being proximate said light source
- a rail, said light source being moveably affixed to a first end of said rail and said second end of said optic fiber being affixed to a second end of said rail, said light source moving along said rail in relation to said second end of said optic fiber,
- at least one filter, each of said at least one filter being affixed to said rail between said light source and said second end of said optic fiber,
- wherein said transmission angle is the angle formed by the center line of said light stream and the surface of said focusing member.

18. The device of claim 17 wherein said light-directing member is a light ring containing a plurality of apertures around an outer periphery, light from said light source exiting through said plurality of apertures in a plurality of streams, each of said plurality of streams being at least one of said transmission angles and a vision aperture, said vision aperture having a periphery less than said outer periphery and being on a direct axis with said user's fovea, thereby enabling said user to maintain vision during said chronotherapy.

19. A method of chronotherapy through the application of artificial light to the retina of a user's eye comprising the steps of applying an artificial light to a user's eye, said artificial light being produced by a remote light source and transmitted to a light directing member by a cladded optic fiber, said light directing member generating a light stream directed at, at least one transmission angle, to the retina of the user's eye, said angle preventing said light from scattering as well as from coming in contact with the user's fovea, wherein said application of said light to said retina prevents damage to said fovea while providing chromotherapeutic benefits and enabling said user almost normal vision.

20. The method of phase shifting a user's circadian clock through the use of a chronotherapy system, said system having;
- a light application device, said light application device having a light source and a light directing member, said light directing member generating a light stream directed at, at least one transmission angle, to the retina of the user's eye, said angle preventing said light from coming in contact with the user's fovea,
- light filtering device, said light filtering device filtering out a narrow melatonin producing wavelength from a user's eyes to inhibit the production of melatonin comprising the steps of:
  - placing said light application device proximate a user's eyes
  - positioning said light application device to enable said light streams to contact said user's retina,
  - exposing said user's retina to said light for a predetermined period of time based on known chronotherapy procedures,
  - placing said light filtering device proximate said user's eyes to inhibit production of melatonin for a predetermined period of time based on known chronotherapy procedures,
  - wherein alternating said application of said light and said filtering device based on known chronotherapy procedures causes said user's circadian clock to phase shift, thereby relieving problems associated with a lack of synchronicity between said user's circadian clock and natural day/night cycles.

* * * * *